US010390950B2

(12) United States Patent
Thomas et al.

(10) Patent No.: US 10,390,950 B2
(45) Date of Patent: Aug. 27, 2019

(54) FLEXIBLE CATHETERS AND METHODS OF FORMING SAME

(71) Applicant: St. Jude Medical, Cardiology Division, Inc., St. Paul, MN (US)

(72) Inventors: Ralph Joseph Thomas, Champlin, MN (US); Sounthara Khouengboua, Chaska, MN (US); Thomas Mark Benson, Minneapolis, MN (US); Brett Allen Hillukka, Hanover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 689 days.

(21) Appl. No.: 14/863,514

(22) Filed: Sep. 24, 2015

(65) Prior Publication Data

US 2016/0095703 A1    Apr. 7, 2016

Related U.S. Application Data

(60) Provisional application No. 62/059,228, filed on Oct. 3, 2014.

(51) Int. Cl.
*A61F 2/966*    (2013.01)
*A61F 2/24*    (2006.01)

(52) U.S. Cl.
CPC ............ *A61F 2/2436* (2013.01); *A61F 2/966* (2013.01); *A61F 2240/001* (2013.01); *A61F 2250/0029* (2013.01)

(58) Field of Classification Search
CPC . A61F 2/2436; A61F 2/966; A61F 2250/0029
See application file for complete search history.

(56) References Cited

U.S. PATENT DOCUMENTS

| 4,423,730 | A | 1/1984 | Gabbay |
| 5,924,424 | A | 7/1999 | Stevens et al. |
| 5,968,068 | A | 10/1999 | Dehdashtian et al. |
| 6,306,141 | B1 | 10/2001 | Jervis |

(Continued)

FOREIGN PATENT DOCUMENTS

| EP | 0812579 A1 | 12/1997 |
| EP | 1129744 A1 | 9/2001 |

(Continued)

OTHER PUBLICATIONS

Supplemental European Search Report for Application No. 15187225.6 dated Mar. 21, 2016.

*Primary Examiner* — Ashley L Fishback
(74) *Attorney, Agent, or Firm* — Lerner, David, Littenberg, Krumholz & Mentlik, LLP

(57) ABSTRACT

A delivery device for a collapsible prosthetic heart valve includes an inner shaft having a proximal end and a distal end, an outer shaft disposed around the inner shaft and longitudinally moveable relative to the inner shaft, and a distal sheath disposed about a portion of the inner shaft and forming a compartment with the inner shaft, the compartment being adapted to receive the prosthetic heart valve. At least one of the outer shaft or the distal sheath may have a pattern of cutouts formed therein, the pattern including at least one ring around a circumference of the at least one of the outer shaft or the distal sheath, the at least one ring having at least one of the cutouts.

9 Claims, 8 Drawing Sheets

(56) References Cited

U.S. PATENT DOCUMENTS

| | | |
|---|---|---|
| 2002/0165600 A1 | 11/2002 | Banas et al. |
| 2006/0106415 A1 | 5/2006 | Gabbay |
| 2006/0142848 A1 | 6/2006 | Gabbay |
| 2006/0167468 A1 | 7/2006 | Gabbay |
| 2007/0005131 A1* | 1/2007 | Taylor .................. A61F 2/2433 623/2.11 |
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0162100 A1 | 7/2007 | Gabbay |
| 2007/0168013 A1 | 7/2007 | Douglas |
| 2007/0203575 A1 | 8/2007 | Forster et al. |
| 2007/0208405 A1 | 9/2007 | Goodin et al. |
| 2007/0239271 A1 | 10/2007 | Nguyen |
| 2008/0147182 A1 | 6/2008 | Righini et al. |
| 2008/0188928 A1* | 8/2008 | Salahieh .......... A61M 25/0054 623/2.11 |
| 2009/0054975 A1 | 2/2009 | del Nido et al. |
| 2009/0171456 A1 | 7/2009 | Kveen et al. |
| 2011/0224678 A1 | 9/2011 | Gabbay |
| 2012/0078351 A1* | 3/2012 | Klima .................. A61F 2/2436 623/2.11 |
| 2014/0343670 A1* | 11/2014 | Bakis .................. A61F 2/2436 623/2.11 |

FOREIGN PATENT DOCUMENTS

| | | |
|---|---|---|
| EP | 1157673 A2 | 11/2001 |
| EP | 1656963 A1 | 5/2006 |
| EP | 3072468 A1 | 9/2016 |
| WO | 10051025 A1 | 5/2010 |
| WO | 10087975 A1 | 8/2010 |
| WO | 2011035327 A1 | 3/2011 |
| WO | 2012023978 A2 | 2/2012 |
| WO | 2012116368 A2 | 8/2012 |

* cited by examiner

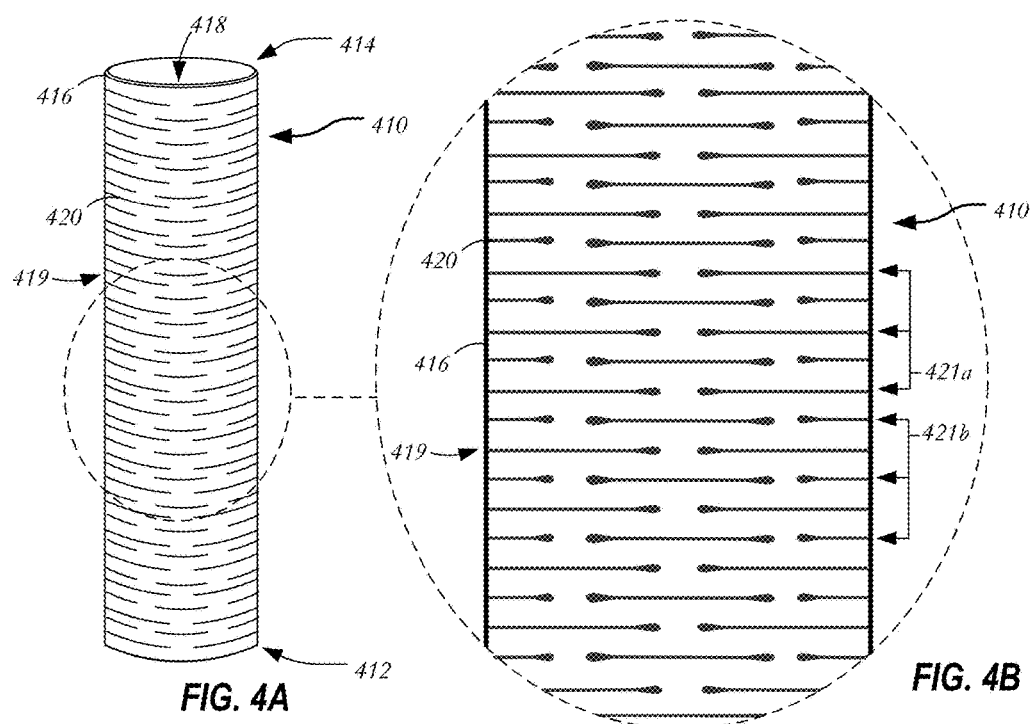
FIG. 4A
FIG. 4B
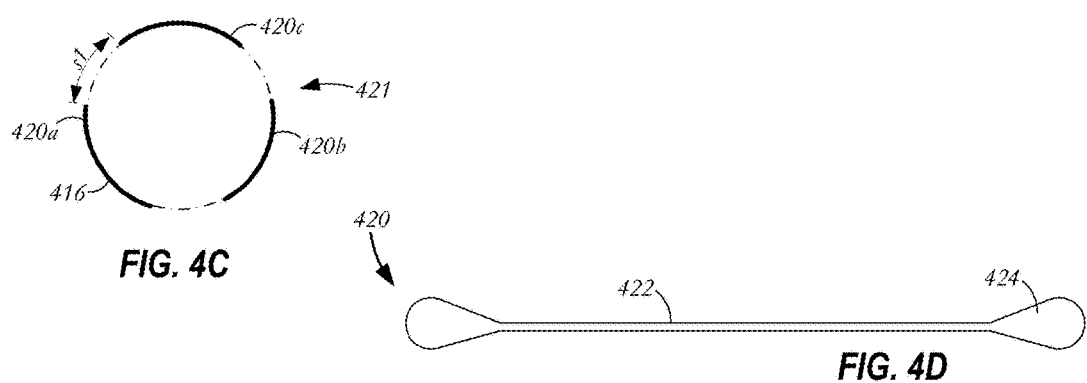
FIG. 4C
FIG. 4D

FLEXIBLE CATHETERS AND METHODS OF FORMING SAME

CROSS-REFERENCE TO RELATED APPLICATIONS

The present application claims the benefit of the filing date of U.S. Provisional Patent Application No. 62/059,228 filed Oct. 3, 2014, the disclosure of which is hereby incorporated herein by reference.

BACKGROUND OF THE INVENTION

The present disclosure relates to delivery devices for implanting medical devices such as prosthetic heart valves and, more particularly, to assemblies and methods for forming delivery devices having greater flexibility.

Prosthetic heart valves may be formed from biological materials such as harvested bovine valves or pericardial tissue. Such valves may include a valve assembly including one or more leaflets and a cuff or skirt, and are typically fitted within a stent, which may be inserted into the heart at the annulus of the compromised native valve to replace the native valve. To perform such an insertion procedure using a minimally invasive technique, it is typically necessary to compress the stent to a reduced diameter for loading into the delivery device.

The delivery device having the prosthetic heart valve loaded therein is advanced through the patient's vasculature until it reaches the implantation site. Due to the size of the arteries and the tortuosity of the delivery route, it may be difficult to maneuver the delivery system to the implantation site. It would therefore be beneficial to provide a delivery device having a greater degree of flexibility that can more readily navigate tortuous paths.

BRIEF SUMMARY OF THE DISCLOSURE

In some embodiments, a delivery device for a collapsible prosthetic heart valve includes an inner shaft having a proximal end and a distal end, an outer shaft disposed around the inner shaft and longitudinally moveable relative to the inner shaft, and a distal sheath disposed about a portion of the inner shaft and forming a compartment with the inner shaft, the compartment being adapted to receive the prosthetic heart valve. At least one of the outer shaft or the distal sheath may have a pattern of cutouts formed therein, the pattern including at least one ring around a circumference of the at least one of the outer shaft or the distal sheath, the at least one ring having at least one of the cutouts.

In some embodiments, a delivery device for a collapsible prosthetic heart valve includes an inner shaft having a proximal end and a distal end, an outer shaft disposed around the inner shaft and longitudinally moveable relative to the inner shaft, and a distal sheath disposed about a portion of the inner shaft and forming a compartment with the inner shaft, the compartment being adapted to receive the prosthetic heart valve. At least one of the outer shaft or the distal sheath may have a pattern of cutouts formed therein, the pattern including a plurality of polygonal cells extending through the at least one of the outer shaft or the distal sheath.

In some embodiments, a method of forming a delivery device for a collapsible prosthetic heart valve includes providing an inner shaft having a proximal end and a distal end, an outer shaft disposed about the inner shaft and being longitudinally moveable relative to the inner shaft, and a distal sheath disposed about a portion of the inner shaft and forming a compartment with the inner shaft, the compartment being adapted to receive the prosthetic heart valve, and cutting a pattern on at least one of the outer shaft or the distal sheath at different axial extents.

BRIEF DESCRIPTION OF THE DRAWINGS

Various embodiments of the present delivery device are disclosed herein with reference to the drawings, wherein:

FIGS. 4A and 4B are a perspective view and an enlarged partial developed view of an outer shaft having a laser cut pattern according to the present disclosure;

FIG. 4C is a schematic representation illustrating the circumferential spacing of cutouts on an outer shaft according to the present disclosure;

FIG. 4D is a schematic developed view of a cutout according to the present disclosure;

DETAILED DESCRIPTION

Figure 1A:
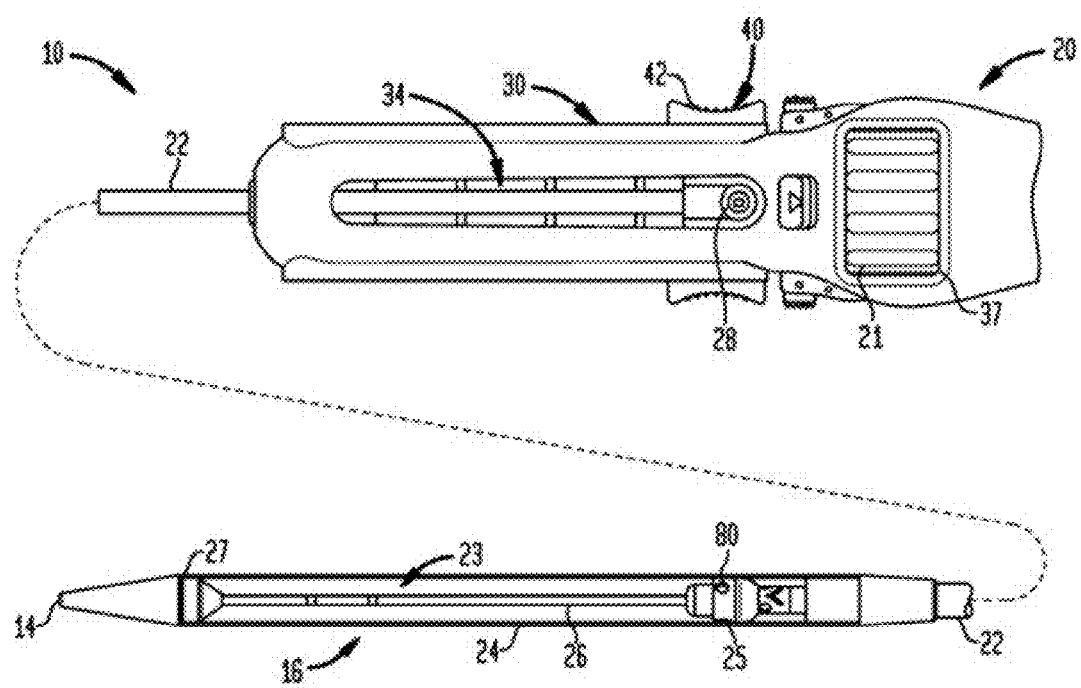
FIG. 1A is a top plan view of a portion of an operating handle of a transfemoral delivery device for a collapsible prosthetic heart valve, shown with a partial longitudinal cross-section of the distal portion of a transfemoral catheter assembly.

Embodiments of the presently disclosed delivery devices are described herein in detail with reference to the drawing figures, wherein like reference numerals identify similar or identical elements. In the description which follows, the term "proximal" refers to the end of a delivery device, or portion thereof, which is closest to the operator in use, while the term "distal" refers to the end of the delivery device, or portion thereof, which is farthest from the operator in use. Also as used herein, the terms "about," "generally" and "approximately" are intended to mean that slight deviations from absolute are included within the scope of the term so modified.

Figure 1B:
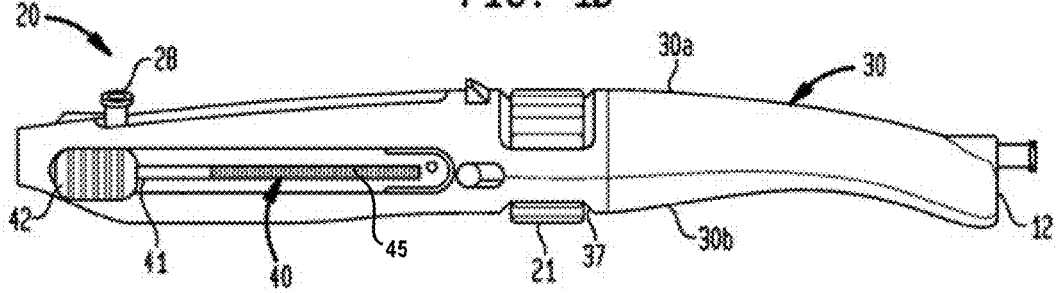
FIG. 1B is a side view of the handle of FIG. 1A.

Referring now to FIGS. 1A-1B to illustrate the structure and function of the present invention, an exemplary transfemoral delivery device 10 for a collapsible prosthetic heart valve (or other types of self-expanding collapsible stents) has a catheter assembly 16 for delivering the heart valve to and deploying the heart valve at a target location, and an operating handle 20 for controlling deployment of the valve from the catheter assembly. Delivery device 10 extends from proximal end 12 (FIG. 1B) to atraumatic tip 14 at the distal end of catheter assembly 16. Catheter assembly 16 is adapted to receive a collapsible prosthetic heart valve (not shown) in compartment 23 defined around inner shaft 26 and covered by distal sheath 24.

Inner shaft 26 may extend from operating handle 20 to atraumatic tip 14 of the delivery device, and includes retainer 25 affixed thereto at a spaced distance from tip 14 and adapted to hold a collapsible prosthetic valve in compartment 23. Retainer 25 may have recesses 80 therein that are adapted to hold corresponding retention members of the valve. Details of the heart valve will be described in greater detail below with reference to FIG. 2. Inner shaft 26 may be made of a flexible material such as braided polyimide or polyetheretherketone (PEEK), for example. Using a material such as PEEK may improve the resistance of inner shaft 26 to kinking while catheter assembly 16 is tracking through the vasculature of a patient.

Distal sheath 24 surrounds inner shaft 26 and is slidable relative to the inner shaft such that it can selectively cover or uncover compartment 23. Distal sheath 24 is affixed at its proximal end to outer shaft 22, the proximal end of which is connected to operating handle 20. Distal end 27 of distal sheath 24 abuts atraumatic tip 14 when the distal sheath is fully covering compartment 23, and is spaced apart from the atraumatic tip when compartment 23 is at least partially uncovered.

Operating handle 20 is adapted to control deployment of a prosthetic valve located in compartment 23 by permitting a user to selectively slide outer shaft 22 proximally or distally relative to inner shaft 26, thereby respectively uncovering or covering the compartment with distal sheath 24. In some examples, operating handle 20 is configured to repeatedly cover or uncover the compartment with distal sheath 24. For example, compartment 23 may be uncovered to expose a valve and allow it to expand at a target location. Once at the location, the functionality and positioning of the valve may be examined prior to complete release of the valve. If the functioning or position of the valve is improper, distal sheath 24 may be advanced to cover the compartment and the valve may be redeployed in a different position or orientation.

Typically, outer shaft 22 may be made of a flexible material such as nylon 11 or nylon 12, and it may have a round braid construction (i.e., round cross-section fibers braided together) or flat braid construction (i.e., rectangular cross-section fibers braided together), for example. The proximal end of inner shaft 26 may be connected in substantially fixed relationship to outer housing 30 of operating handle 20, and the proximal end of outer shaft 22 may be affixed to carriage assembly 40 that is slidable along a longitudinal axis of the handle housing, such that a user can selectively slide the outer shaft relative to the inner shaft by sliding the carriage assembly relative to the handle housing. A hemostasis valve 28 may be provided and may include an internal gasket adapted to create a seal between inner shaft 26 and the proximal end of outer shaft 22.

Handle housing 30 includes a top portion 30a and a bottom portion 30b. The top and bottom portions 30a and 30b may be individual pieces joined to one another as shown in FIG. 1B. Collectively, top and bottom portions 30a and 30b define elongated space 34 in housing 30 in which carriage assembly 40 may travel. Elongated space 34 preferably permits carriage assembly 40 to travel a distance that is at least as long as the anticipated length of the prosthetic valve to be delivered (e.g., at least about 50 mm), such that distal sheath 24 can be fully retracted from around the prosthetic valve. Carriage assembly 40 may further include a pair of carriage grips 42 each attached to body portion 41 by a respective carriage grip shaft (not shown).

Handle housing 30 further defines a pocket 37 that extends through the top portion 30a and bottom portion 30b for receiving a deployment actuator 21. Deployment actuator 21 is internally threaded for selective engagement with a threaded rod 45. When the deployment actuator 21 is in threaded engagement with the threaded rod, rotation of the deployment actuator in one direction (either clockwise or counterclockwise depending on the orientation of the threads on the threaded rod) causes the threaded rod to move proximally, at the same time pulling the body portion 41 of carriage assembly 40 proximally through elongated space 34, and pulling outer shaft 22 and distal sheath 24 proximally relative to inner shaft 26. Similarly, when deployment actuator 21 is in threaded engagement with the threaded rod, rotation of the deployment actuator in the opposite direction causes the threaded rod to move distally, at the same time pushing body portion 41 of carriage assembly 40 distally through elongated space 34, and pushing outer shaft 22 and distal sheath 24 distally relative to inner shaft 26.

Figure 2:
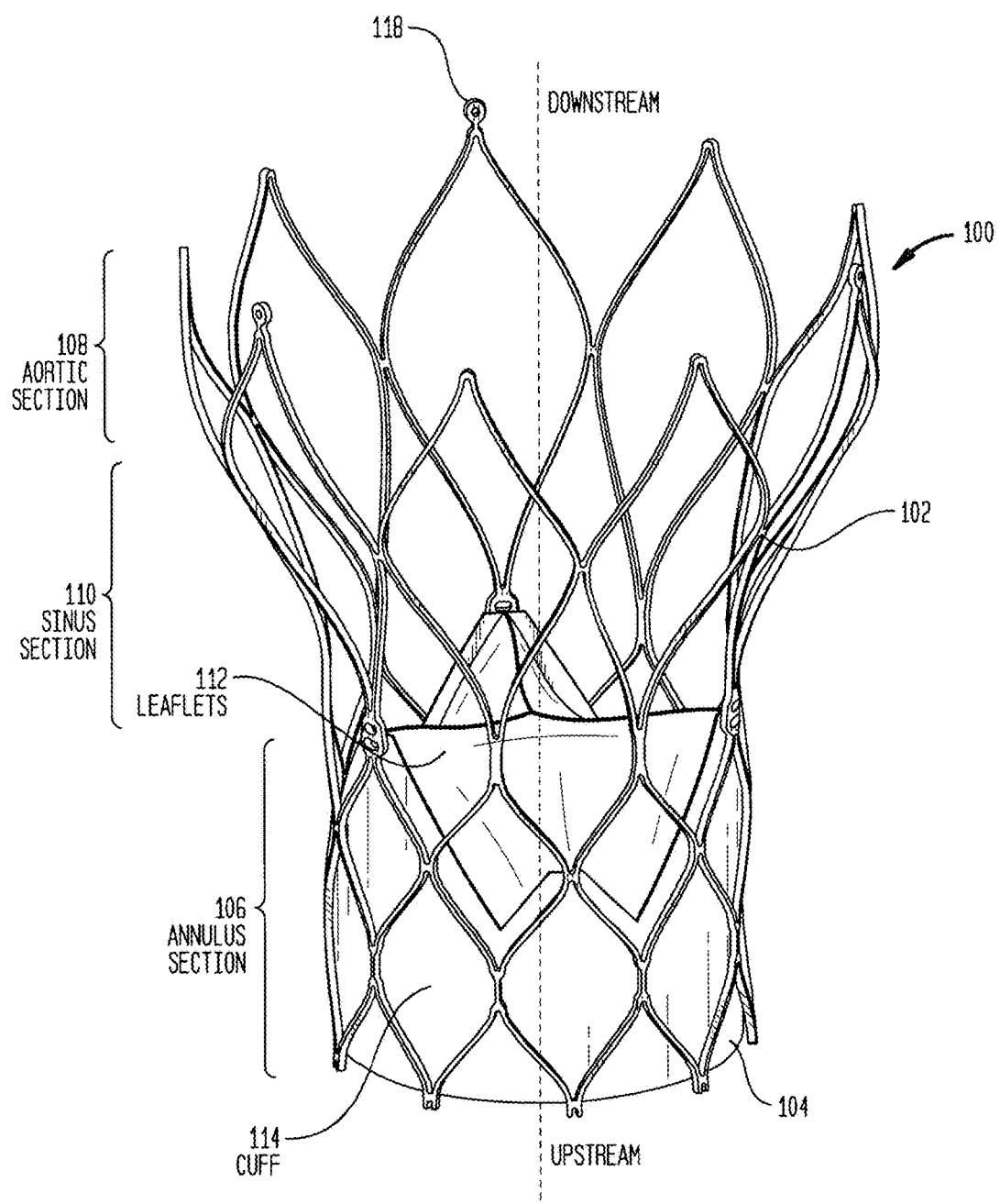
FIG. 2 is a perspective view of a self-expanding prosthetic heart valve.

FIG. 2 shows a bioprosthetic valve 100 such as that described in U.S. Patent Publication No. 2012/0053681, the contents of which are hereby incorporated herein by reference. Prosthetic valve 100 is designed to replace a native aortic valve. Valve 100 has a collapsed condition and an expanded condition and may be formed from a collapsible framework or stent 102, with valve assembly 104 internally connected to the stent. Stent 102 may be formed from any suitable biocompatible material, such as nitinol or any other suitable elastic or shape memory material, and may include annulus section 106, aortic section 108, and sinus section 110 located between the annulus section and the aortic section. Aortic section 108 may have a larger cross-section than annulus section 106. Valve assembly 104 includes a plurality of leaflets 112 and cuff 114 attached to stent 102. Leaflets 112 and cuff 114 may be formed from a biocompatible polymer, from natural tissue such as bovine or porcine pericardial tissue, or from other appropriate biocompatible materials. Valve assembly 104 is preferably connected to stent 102 generally within annulus section 106. A plurality of tabs or retainers 118 may be spaced around one or both ends of stent 102 for engagement with recesses 80 of retainer 25, described above. Retainers 118 may also be utilized to collapse valve 100 for loading into delivery device 10.

Valve 100 is preferably stored in its expanded or open condition as bioprosthetic valve assembly 104 may be compromised by storage in a collapsed condition for extended periods of time. As such, it is necessary to crimp valve 100 into a collapsed condition of reduced cross-section for loading into delivery device 10 just prior to the surgical implantation procedure. In order to effectively limit the time period valve 100 is collapsed, the crimping process is preferably conducted in the operating arena by the surgeon, interventional cardiologist or surgical assistant using a specialized assembly.

Figure 3:
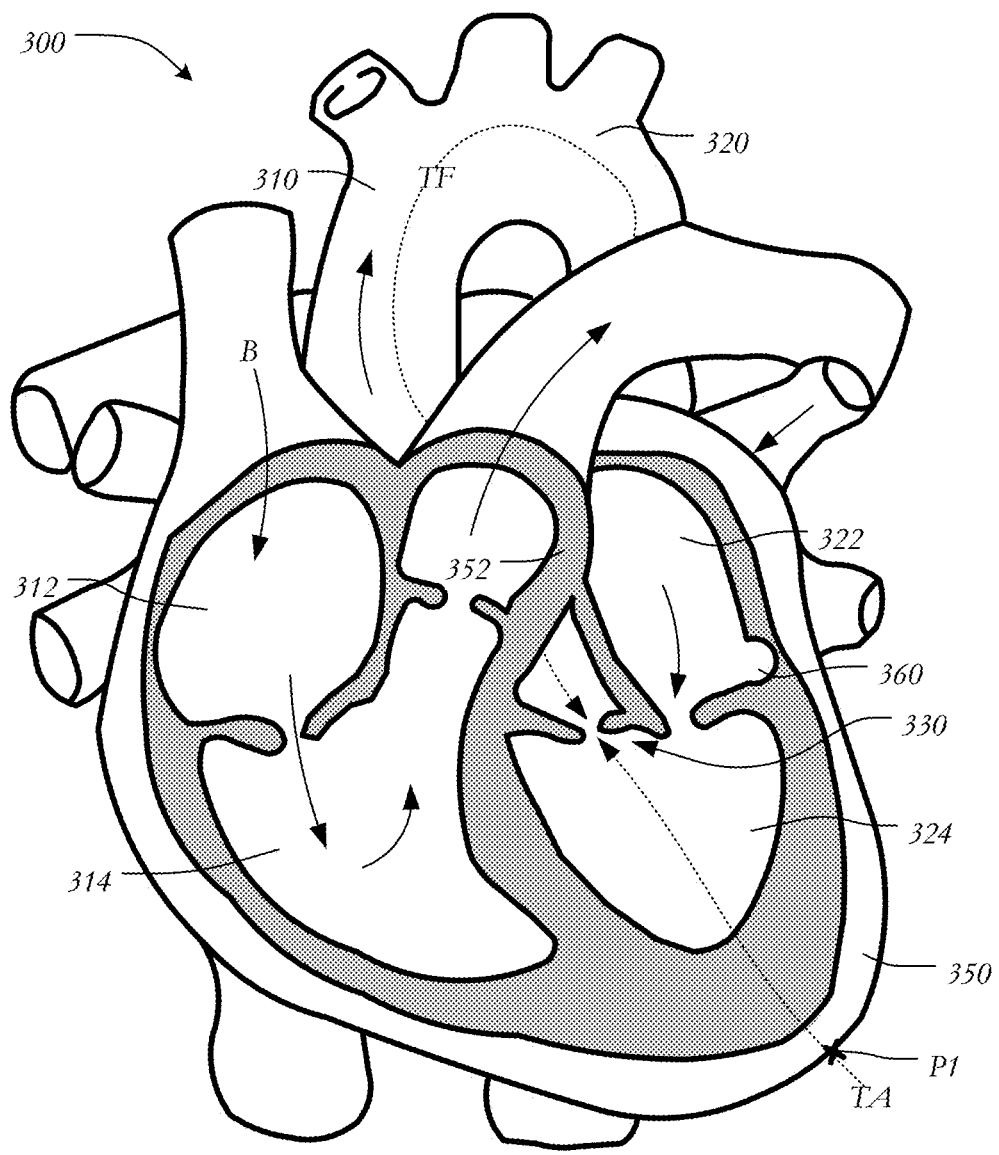
FIG. 3 is a schematic representation of a human heart showing transapical and transfemoral delivery approaches.

FIG. 3 is a schematic representation of a human heart 300. The human heart includes two atria and two ventricles: a right atrium 312 and a left atrium 322, and a right ventricle 314 and a left ventricle 324. As illustrated in FIG. 3, heart 300 further includes an aorta 310, and an aortic arch 320. Disposed between left ventricle 324 and aorta 310 is aortic valve 330. During ventricular systole, pressure rises in left ventricle 324. When the pressure in the left ventricle rises above the pressure in aorta 310, aortic valve 330 opens, allowing blood to exit left ventricle 324 into the aorta 310. When ventricular systole ends, pressure in left ventricle 324 rapidly drops. When the pressure in left ventricle 324 decreases, the aortic pressure forces aortic valve 330 to close. Blood flows through heart 300 in the direction shown by arrows "B".

A dashed arrow, labeled "TF", indicates a transfemoral approach for treating or replacing heart tissue using a delivery device, such as that shown in FIGS. 1A-C. In transfemoral delivery of an aortic valve, an incision is made adjacent the hip and threaded up the femoral artery and around the aortic arch as shown. A dashed arrow, labeled "TA", indicates a transapical approach for treating or replacing heart tissue. In transapical delivery, a small incision is made between the ribs and into the apex of the left ventricle 324 at position "P1" in heart wall 350 to deliver the prosthetic heart valve to the target site. In order to more easily advance a catheter to a target site using either of these approaches, or any other approach, a catheter with greater flexibility than conventional catheters may preferably be employed.

In order to increase the flexibility of the delivery system, an outer shaft of a delivery device may be laser cut in a repeating pattern. As shown in FIG. 4A, outer shaft 410 is formed of a generally cylindrical hypotube having proximal end 412 and distal end 414. Outer shaft 410 may be formed of a metal, such as nitinol, Elgiloy, or stainless steel, or a biocompatible polymer. Outer shaft 410 may have a size of approximately 24 French or less with outer wall 416 defining lumen 418 extending therethrough from proximal end 412 to distal end 414.

Portions of outer wall 416 may be removed to form cutouts 420, for example, by laser cutting. As shown in the enlargement of FIG. 4B, multiple cutouts 420 may be made to form a repeating pattern 419. For example, three cutouts 420a, 420b, 420c may be formed in outer wall 416 about the circumference of outer shaft 410, each cutout being spaced from adjacent cutouts by a distance s1 to form a discontinuous ring 421 about the circumference at a given longitudinal extent (FIG. 4C). As used herein, the term "ring" is used to describe any number of cutouts aligned with one another about the circumference of a body, and is not limited to a single cutout that forms a complete circle about the circumference of the body. The number of cutouts 420 per ring 421 may vary as desired and may include as few as one or two cutouts 420 or as many as four, five, six or more cutouts 420.

Multiple rings 421 may be formed along the length of outer shaft 410. In the example shown, rings 421 are divided into two sets, a first set of rings 421a and a second set of rings 421b. Rings of the first set of rings 421a may all be aligned with one another along the length of outer shaft 410 as shown, and rings of the second set of rings 421b may be offset from the first set of rings 421a by a predetermined radial angle (e.g., offset by 90 degrees). Successive rings may be chosen such that the rings alternate between the two sets as shown. Though two sets are shown, it will be understood that the rings may be formed in any number of sets, for example, three, four or five sets, that are circumferentially offset from one another.

Turning now to FIG. 4D, the details of cutouts 420 will be more fully described. As shown, each cutout 420 includes an elongated portion 422 and a pair of teardrop portions 424 on opposing ends of the elongated portion 422. The combined length of the cutouts 420 around each ring may make up between about 50% and about 90% of the circumference of outer shaft 410. In this example, cutouts 420 are disposed perpendicular to the longitudinal axis of outer shaft 410. Teardrop portions 424 may provide added flexion for outer shaft 410, while providing strain relief and maintain adequate compression resistance of outer shaft 410. In some examples, each cutout 420 includes a teardrop portion 424 at only one end of elongated portion 422. In other examples, cutouts 420 may include portions of other shapes such as triangles, circles, semicircles, or the like at one or both ends of elongated portion 422, instead of teardrop portions 424.

Variations of the embodiment of FIGS. 4A-4D are possible depending on the length and/or diameter of the outer shaft, the materials chosen for forming the shaft and other considerations. For example, cutouts 420 may include a combination of shapes discussed above. The number of rings 421 cut into outer shaft 410 may also be varied. In some examples, outer shaft 410 includes between about 40 and about rings 421. Additionally, the axial distance between adjacent rings 421 may be between about 0.3 mm and about 1 mm. Rings 421 may be spaced from one another evenly or unevenly in the axial direction. Each ring 421 may also include the same or a different number of cutouts 420. For example, a first ring may include only two cutouts, while an adjacent ring includes three cutouts.

Either the same, a similar or a different pattern of rings may also be laser cut into the distal sheath of a delivery device. Thus, the distal sheath and/or outer shaft may be laser cut as shown to increase the flexibility of the delivery device over current devices of a similar size, while maintaining comparable compression resistance needed for resheathability. Thus, by providing a continuous wall of an outer shaft from one end to the other, the wall having a plurality of cutouts, comparable compression strength is maintained while flexibility is increased.

Figure 5B:
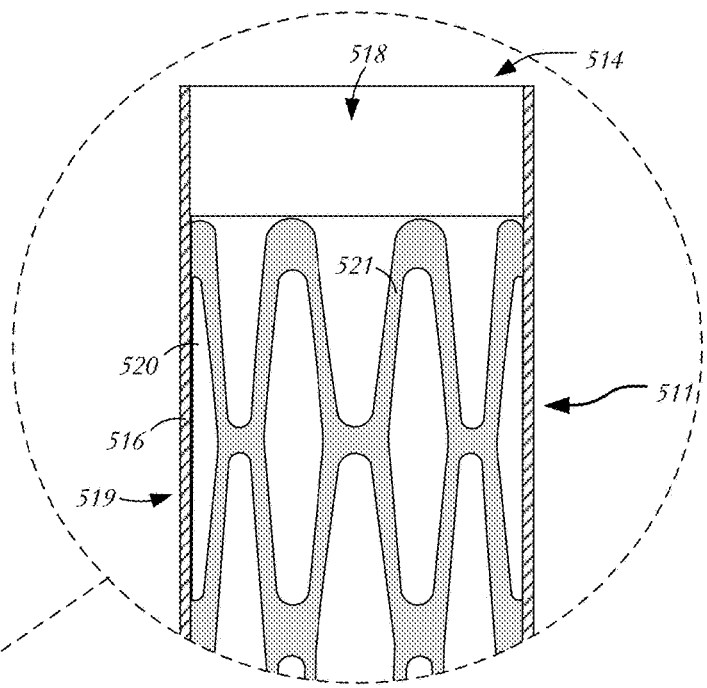
FIGS. 5A and 5B are a front view and an enlarged partial view of a laser cut distal sheath according to the present disclosure.
Figure 5A:
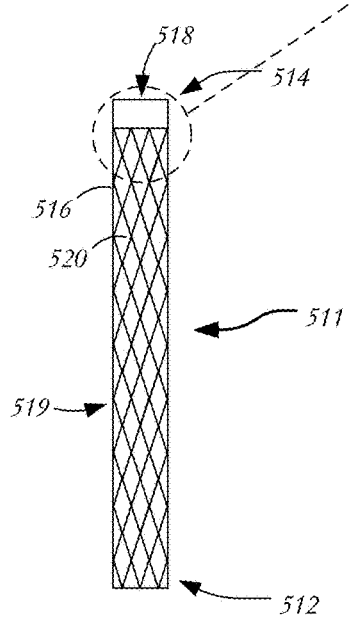

FIGS. 5A and 5B illustrate an embodiment of a distal sheath of a delivery device having improved flexibility over conventional distal sheaths. In this example, a pattern 519 is cut into distal sheath 511 of a delivery device. It will be understood that the same or similar pattern may also be formed in the outer shaft of the delivery device or in both the distal sheath and the outer shaft. Distal sheath 511 is formed of a generally cylindrical hypotube having proximal end 512 and distal end 514. Distal sheath 511 may be formed of a metal, such as nitinol, Elgiloy, or stainless steel, or a biocompatible polymer. Distal sheath 511 may have a size of approximately 24 French or less and may include outer wall 516 defining lumen 518 extending therethrough from proximal end 512 to distal end 514.

Instead of forming elongated cutouts 420, polygonal cutouts, hereinafter referred to as cells 520, may be cut in outer wall 516 of distal sheath 511 to form pattern 519 having a stent-like structure (FIG. 5B). In forming cells 520, struts 521 remain about each cell 520, the struts being flexible and aiding in the maneuverability of distal sheath 511. Thus, certain cells 520 may compress at portions of the distal sheath while other cells expand at other portions of the distal sheath when the distal sheath 511 is bent. In one example, cells 520 are substantially diamond-shaped, with each cell being defined by four struts 521. In at least some examples, the length of each cell in the axial direction of distal sheath 511 is between about 0.5 mm and about 5 mm when distal sheath 511 is substantially straight. The number of cells formed in the distal sheath may be varied. In some examples, three, four, five or six cells may be formed about the circumference of outer wall 516 at a given longitudinal extent of the distal sheath. Also, the number of rows of cells axially disposed along the length of distal sheath 511 may vary. Generally, the smaller the cells in the axial direction and the greater the number of rows of cells, the greater the amount of flexibility that will be imported to distal sheath 511.

Figure 6:
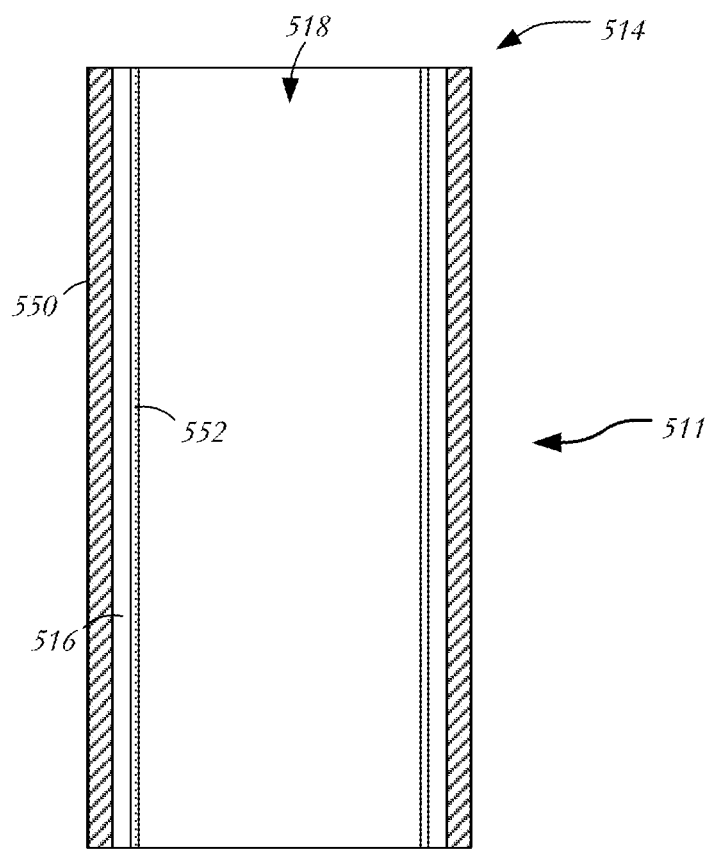
FIG. 6 is a schematic longitudinal cross-section of a distal sheath according to the present disclosure.

After cutting pattern 519 into outer wall 516 of distal sheath 511, a polymer jacket 550 may be added to the abluminal (i.e., outer) surface of outer wall 516 in order to increase the column strength of distal sheath 511 and prevent blood/debris from impinging on the valve (FIG. 6). Polymer jacket 550 may be formed of any suitable biocompatible polymer, including polyether block amide (e.g., PEBAX®), nylons, polyester resins, urethanes or suitable combinations thereof. A non-polymeric material may also be used to form jacket 550. Additionally, a liner 552, such as a polytetrafluoroethylene (PTFE) liner, may be added to the luminal (i.e., inner) surface of outer wall 516 to add lubricity to portions of the outer wall 516 that may contact the heart valve in compartment 23 of the delivery device.

Thus, after a pattern is cut into outer wall 516 of distal sheath 511, the distal sheath still has enough column strength to be able to resheath a transcatheter aortic replacement valve while being flexible enough to traverse body tissue to the target location. For example, in transfemoral delivery, the distal sheath 511 is capable of more easily crossing the aortic arch and aligning with the native aortic annulus. Having distal sheath 511 formed of nitinol or another suitable material that is laser cut in this fashion provides the requisite column strength and flexibility. Additionally, wall 516 may be made thinner compared to traditional braided constructions because the conventional braided wires overlap one another, adding to the overall wall thickness.

Figure 7:
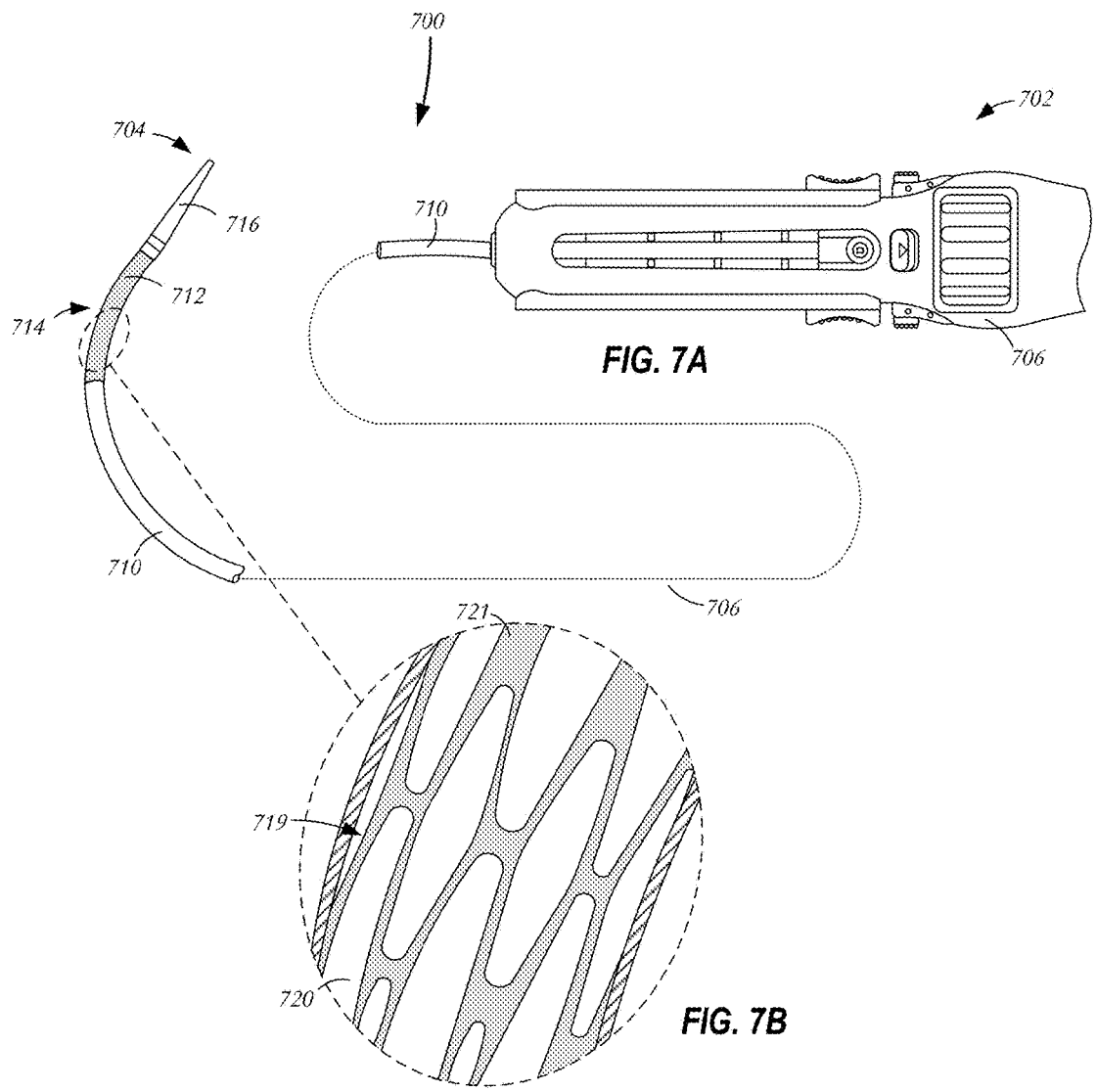
FIG. 7A is a schematic top plan view showing the bending of a distal sheath.
FIG. 7B is an enlarged partial view showing the bending of the struts of the distal sheath of FIG. 7A.

FIGS. 7A and 7B illustrate the use of delivery device 700 having features of the present disclosure to deliver a medical device, such as a prosthetic heart valve, to an implant location. Delivery device 700 may include all of the features discussed above with reference to FIGS. 1-3 and generally has proximal end 702 and distal end 704. Delivery device 700 includes operating handle 706 for use by a physician or operator coupled at one side to outer shaft 710, which in turn extends to slidable distal sheath 712, forming compartment 714 therein for housing a prosthetic heart valve (not shown) disposed about an inner shaft (also not shown). The delivery device 700 further includes a conical distal tip 716 at distal end 704. As shown in the enlargement of FIG. 7B, the laser cut pattern 719 (e.g., the process of cutting cells 720 with struts 721) in distal sheath 714 allows the distal sheath to easily bend during use, making the implantation process easier and quicker. The same or a similar pattern may, likewise, be cut into outer shaft 710 instead of, or in addition to, the pattern cut into distal sheath 714.

Figure 8:
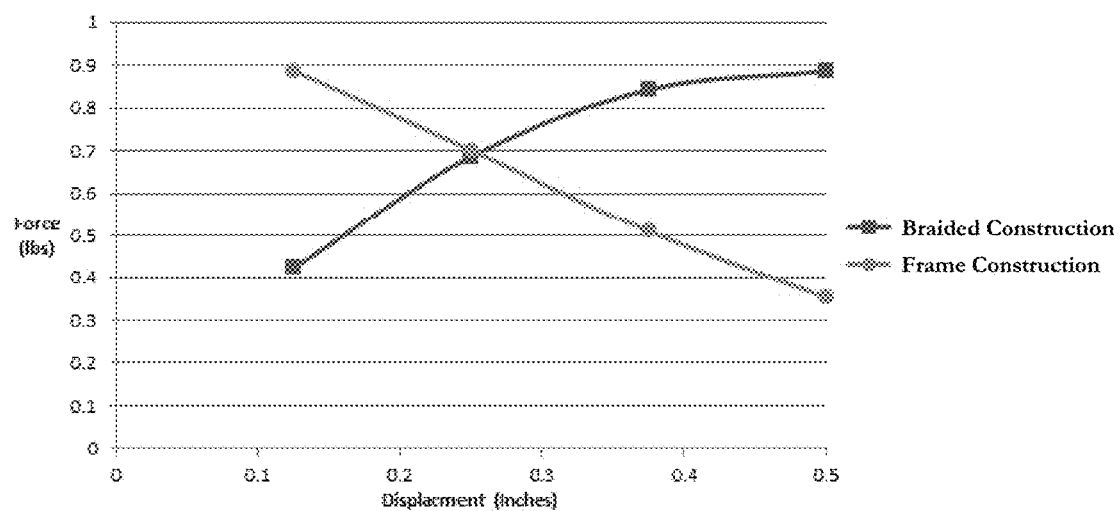
FIG. 8 is a three-point bend comparison of a conventional braided distal sheath and a distal sheath formed according to the present disclosure.

FIG. 8 is a comparison between a conventional distal sheath formed of braided construction and a laser-cut sheath formed with pattern 519 of FIGS. 5A and 5B. In this comparison, a three-point bend test was performed on the two sheaths to displace a midpoint of each sheath between 0 and 0.5 inches. In this illustration, the two end points of each sheath were disposed about 3 inches apart. As seen from the comparison, almost 0.9 pounds of force is required to displace the midpoint of a sheath of braided construction a distance of 0.5 inches. Conversely, to displace the midpoint of a distal sheath having a laser-cut pattern 519 a distance of 0.5 inches, less than 0.4 pounds of force is required. Thus, the frame construction of FIGS. 5A and 5B requires less than half of the force of the braided construction for a displacement of 0.5 inches. This flexible construction reduces the risk of trauma to body tissue during delivery around tight turns.

Numerous modifications may be made to the illustrative embodiments and other arrangements may be devised without departing from the spirit and scope of the present disclosure as defined by the appended claims. For example, though the delivery system has been shown as a transfemoral delivery system, it will be understood that the teachings of the present disclosure are not so limited and that similar patterns may be cut into the outer sheath and/or distal sheath of transapical, transseptal or other delivery systems. Additionally, while the examples have been shown for a delivery system for transcatheter aortic valve replacement, the disclosed teachings are equally applicable for other valve replacement, such as, for example, mitral valve replacement, as well as for other catheters for valve replacement and/or repair. Moreover, the present disclosure may also be applied to catheters for other medical purposes, such as the implantation of stents and other medical devices, other types of percutaneous or laparoscopic surgical procedures and the like.

In some embodiments, a delivery device for a collapsible prosthetic heart valve includes an inner shaft having a proximal end and a distal end, an outer shaft disposed around the inner shaft and longitudinally moveable relative to the inner shaft, and a distal sheath disposed about a portion of the inner shaft and forming a compartment with the inner shaft, the compartment being adapted to receive the prosthetic heart valve. At least one of the outer shaft or the distal sheath may have a pattern of cutouts formed therein, the pattern including at least one ring around a circumference of the at least one of the outer shaft or the distal sheath, the at least one ring having at least one of the cutouts.

In some examples, the pattern includes a plurality of rings disposed along a longitudinal axis of the outer shaft or the distal sheath; and/or the plurality of rings may include a first set of rings having a first pattern and a second set of rings having a second pattern, the first pattern, the first set of rings being offset from the second pattern by a predetermined angle in the circumferential direction; and/or the first pattern may be offset from the second pattern by 90 degrees; and/or successive rings may alternate between a ring from the first set of rings and a ring from the second set of rings; and/or the at least one ring may include multiple discontinuous cutouts aligned with one another at a predetermined position along a longitudinal axis of the outer shaft in the distal sheath; and/or the at least one ring may include three discontinuous cutouts; and/or the at least one cutout may include an elongated portion and two teardrop portions on opposing ends of the elongated portion; and/or at least one of the outer shaft or the distal sheath may include stainless steel.

In some embodiments, a delivery device for a collapsible prosthetic heart valve includes an inner shaft having a proximal end and a distal end, an outer shaft disposed around the inner shaft and longitudinally moveable relative to the inner shaft, and a distal sheath disposed about a portion of the inner shaft and forming a compartment with the inner shaft, the compartment being adapted to receive the prosthetic heart valve. At least one of the outer shaft or the distal sheath may have a pattern of cutouts formed therein, the pattern including a plurality of polygonal cells extending through the at least one of the outer shaft or the distal sheath.

In some examples, the plurality of polygonal cells may include diamond-shaped cells; and/or the pattern may be formed in the distal sheath; and/or may further include a liner disposed on a luminal surface of the distal sheath; and/or may further include a polymer jacket disposed on an abluminal surface of the distal sheath; and/or at least one of the outer shaft or the distal sheath may include stainless steel.

In some embodiments, a method of forming a delivery device for a collapsible prosthetic heart valve includes providing an inner shaft having a proximal end and a distal end, an outer shaft disposed about the inner shaft and being longitudinally moveable relative to the inner shaft, and a distal sheath disposed about a portion of the inner shaft and forming a compartment with the inner shaft, the compartment being adapted to receive the prosthetic heart valve, and cutting a pattern on at least one of the outer shaft or the distal sheath at different axial extents.

In some examples, cutting a pattern may include forming at least one cutout having an elongated portion and two teardrop portions on opposing ends of the elongated portion; and/or the at least one cutout may include a plurality of cutouts arranged in a ring; and/or cutting a pattern may include forming at least one polygonal cutout on an outer surface of at least one of the outer shaft and the distal sheath; and/or the at least one polygonal cutout may include a plurality of diamond-shaped cells.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for a collapsible prosthetic heart valve comprising:
    an inner shaft having a proximal end and a distal end;
    an outer shaft disposed around the inner shaft and longitudinally moveable relative to the inner shaft; and
    a distal sheath disposed about a portion of the inner shaft and forming a compartment with the inner shaft, the compartment being adapted to receive the prosthetic heart valve;
    the outer shaft having a pattern of cutouts formed therein, the pattern including at least one ring around a circumference of the outer shaft, the at least one ring having at least one of the cutouts.

2. The delivery device of claim 1, wherein the pattern includes a plurality of rings disposed along a longitudinal axis of the outer shaft.

3. The delivery device of claim 2, wherein the plurality of rings include a first set of rings having a first pattern and a second set of rings having a second pattern, the first pattern, the first set of rings being offset from the second pattern by a predetermined angle in the circumferential direction.

4. The delivery device of claim 3, wherein the first pattern is offset from the second pattern by 90 degrees.

5. The delivery device of claim 3, wherein successive rings alternate between a ring from the first set of rings and a ring from the second set of rings.

6. The delivery device of claim 1, wherein the at least one ring includes multiple discontinuous cutouts aligned with one another at a predetermined position along a longitudinal axis of the outer shaft.

7. The delivery device of claim 6, wherein the at least one ring includes two discontinuous cutouts.

8. The delivery device of claim 1,
    wherein the at least one cutout includes an elongated portion and two teardrop portions on opposing ends of the elongated portion.

9. The delivery device of claim 1, wherein at least one of the outer shaft or the distal sheath comprises stainless steel.

* * * * *